United States Patent
Limem et al.

(10) Patent No.: US 11,612,754 B2
(45) Date of Patent: Mar. 28, 2023

(54) RESORBABLE NONWOVEN POUCHES FOR MEDICAL DEVICE IMPLANTS

(71) Applicant: Tepha, Inc., Lexington, MA (US)

(72) Inventors: Skander Limem, Melrose, MA (US);
David Martin, Lexington, MA (US);
Said Rizk, Windham, NH (US); Simon F. Williams, Lexington, MA (US)

(73) Assignee: Tepha, Inc., Lexington, MA (US)

(*) Notice: Subject to any disclaimer, the term of this patent is extended or adjusted under 35 U.S.C. 154(b) by 202 days.

(21) Appl. No.: 16/553,651

(22) Filed: Aug. 28, 2019

(65) Prior Publication Data

US 2020/0197712 A1 Jun. 25, 2020

Related U.S. Application Data

(60) Provisional application No. 62/784,244, filed on Dec. 21, 2018.

(51) Int. Cl.
*A61K 31/00* (2006.01)
*A61K 31/195* (2006.01)
(Continued)

(52) U.S. Cl.
CPC .......... *A61N 1/37512* (2017.08); *A61K 31/00* (2013.01); *A61K 31/195* (2013.01);
(Continued)

(58) Field of Classification Search
None
See application file for complete search history.

(56) References Cited

U.S. PATENT DOCUMENTS 5,458,653 A 10/1995 Davidson
6,548,569 B1 4/2003 Williams et al.
(Continued)

FOREIGN PATENT DOCUMENTS

EP 1 676 591 B1 8/2018
WO 2004071485 A1 8/2004
(Continued)

OTHER PUBLICATIONS

Valente et al., "Effect of sterilization methods on electrospun poly(lactic acid) (PLA) fiber alignment for biomedical applications" (2016), ACS Applied Materials and Interfaces, 8 (5), 3241-3249. (Year: 2016).*
(Continued)

*Primary Examiner* — Johann R Richter
*Assistant Examiner* — Casey S Hagopian
(74) *Attorney, Agent, or Firm* — Wolf, Greenfield & Sacks, P.C.

(57) ABSTRACT

Nonwoven resorbable pouches that at least partially enclose implantable medical devices and improved methods for producing the implantable medical device pouches are described. The nonwoven pouches may comprise one or more drugs. Implantable medical devices that are placed in the pouches prior to implantation are prevented from migrating from the site of implantation by tissue ingrowth into the pouch. Antibiotics may be incorporated into the pouches to prevent post-operative infections. The pouches may be formed in fewer steps than conventional pouches, and without polymer coatings. Nonwoven pouches can be formed in one step by dry spinning instead of using multiple processing steps. In embodiments, the nonwoven pouches are smoother on the inside than the outside to tightly fit the implantable medical devices internally while encouraging external tissue ingrowth. In embodiments, the nonwoven (Continued)

pouches eliminate the use of knitted or woven multifilament fibers that can trap bacteria and result in post-operative infection.

14 Claims, 3 Drawing Sheets

(51) Int. Cl.
    *A61K 31/496*     (2006.01)
    *A61L 31/14*     (2006.01)
    *A61L 31/16*     (2006.01)
    *A61B 17/00*     (2006.01)
    *A61B 50/30*     (2016.01)
    *A61N 1/375*     (2006.01)

(52) U.S. Cl.
    CPC .......... *A61K 31/496* (2013.01); *A61L 31/148* (2013.01); *A61L 31/16* (2013.01); *A61B 50/30* (2016.02); *A61B 2017/00004* (2013.01); *A61B 2050/314* (2016.02)

(56) References Cited

U.S. PATENT DOCUMENTS

| | | | |
|---|---|---|---|
| 8,315,700 | B2 | 11/2012 | Citron et al. |
| 8,591,531 | B2 | 11/2013 | Buevich et al. |
| 8,636,753 | B2 | 1/2014 | Buevich et al. |
| 8,911,765 | B2 | 12/2014 | Moses et al. |
| 9,023,114 | B2 * | 5/2015 | Buevich ................ A61N 1/375 |
| | | | 623/23.75 |
| 9,457,129 | B2 | 10/2016 | Buevich et al. |
| 9,480,780 | B2 | 11/2016 | Martin et al. |
| 9,486,560 | B2 | 11/2016 | Buevich et al. |
| 9,848,955 | B2 | 12/2017 | Buevich et al. |
| 9,987,116 | B2 | 6/2018 | Buevich et al. |
| 2008/0128315 | A1 * | 6/2008 | Buevich ................ A61L 31/148 |
| | | | 514/254.1 |
| 2008/0132922 | A1 | 6/2008 | Buevich et al. |
| 2008/0305144 | A1 * | 12/2008 | Brown ................ A61L 27/502 |
| | | | 523/113 |
| 2009/0264472 | A1 * | 10/2009 | Wohabrebbi ............ A61P 25/04 |
| | | | 514/330 |
| 2011/0046729 | A1 | 2/2011 | Schuessler et al. |
| 2012/0041555 | A1 * | 2/2012 | Manesis .................... A61F 2/12 |
| | | | 427/2.24 |
| 2012/0058100 | A1 | 3/2012 | Shastri et al. |
| 2016/0082160 | A1 | 3/2016 | Martin et al. |

FOREIGN PATENT DOCUMENTS

| | | |
|---|---|---|
| WO | 2005058414 A1 | 6/2005 |
| WO | 2005061003 A1 | 7/2005 |
| WO | 2008127411 A1 | 10/2008 |
| WO | 2008136856 A3 | 12/2008 |
| WO | 2009113972 A2 | 9/2009 |
| WO | 2011159784 A1 | 12/2011 |
| WO | 2016048950 A1 | 3/2016 |

OTHER PUBLICATIONS

Kantrowitz, A reporton an implantable electronic cardiac pacemaker, Geriatrics, 22:101-105 (1967).
Parsonnet, A stretch fabric pouch for implanted pacemakers, Arch Surg, 105:654-656 (1972).
PCT/US10/48645 Search Report and Written Opinion, dated Nov. 13, 2019.
Zoll et al., Four-year experience with an implantable cardiac pacemaker, Ann. Surg., 160(3): 351-362 (1964).
Extended European Search Report dated Aug. 8, 2022 for European Application No. EP 19901373.1.

* cited by examiner

RESORBABLE NONWOVEN POUCHES FOR MEDICAL DEVICE IMPLANTS

RELATED APPLICATIONS

The present application claims priority to U.S. Ser. No. 62/784,244, filed Dec. 21, 2018, the entirety of which is incorporated herein by reference for all purposes.

FIELD OF THE INVENTION

The present invention generally relates to implantable medical devices, and more particularly to pouches enclosing the implantable medical devices.

BACKGROUND OF THE INVENTION

Pouches for encasing implantable medical devices have become an important part of procedures to implant pacemakers. The pouches help secure the pacemaker in position, and prevent it from migrating away from the implantation site. Antibiotic coatings on the exterior surface of the pouches can help prevent post-operative infection particularly resulting from surgical site contamination.

Descriptions of pouches for use with pacemakers and other implantable medical devices are set forth in various publications including, for example, Zoll et al., Four-year experience with an implantable cardiac pacemaker, Ann. Surg., 160(3): 351-362 (1964); Kantrowitz, A report on an implantable electronic cardiac pacemaker, Geriatrics, 22:101-105 (1967); and Parsonnet, A stretch fabric pouch for implanted pacemakers, Arch Surg, 105:654-656 (1972). See also International Patent Nos. WO 2005/061003 and WO 2005/058414, both to Cobian; and US Publication Nos. 2008/0132922 and 2008/0128315, both to Buevich.

Notwithstanding the foregoing, an improved pouch, and method of making same, having features, steps, and advantages as described herein is still desirable.

SUMMARY OF THE INVENTION

Embodiments of the invention include resorbable nonwoven pouches that at least partially enclose or encase implantable medical devices.

In embodiments, the pouches eliminate one or more manufacturing steps used in the preparation of existing pouches, and also eliminate the use of knitted or woven multifilament fibers that can trap bacteria and result in post-operative infection. The pouches described herein may be produced by spinning of nonwoven in a single step, rather than by extruding polymeric monofilament fiber or multifilament fiber, and knitting or weaving those fibers to form a pouch. Furthermore, an additional step in the manufacture of resorbable nonwoven pouches comprising one or more bioactive agents may be eliminated by simultaneously incorporating one or more bioactive agents in the nonwoven structure of the pouch as it is formed. This method eliminates the need to first produce a pouch, and then coat it with one or more bioactive agents, or a polymer comprising one or more bioactive agents. In embodiments, methods eliminate the need for the pouch to be coated with a polymer coating.

Implantable medical devices that may be at least partially enclosed or encased by the nonwoven resorbable pouches include cardiac rhythm management devices (CRM's), pacemakers, defibrillators, pulse generators, implantable access systems, muscle and nerve stimulators, cochlear implants, ventricular assist devices, gastric stimulators, infusion pumps, drug pumps, neurostimulators, vagal nerve stimulators, spinal cord neuromodulators, deep brain stimulators, and sacral nerve stimulators. Examples of CRM devices and their dimensions are described in US Publication No. 2008/0132922 to Buevich, incorporated herein by reference in its entirety. The nonwoven resorbable pouches may also be used to partially enclose or fully encase breast implants.

In accordance with the subject invention, the pouches are preferably porous and permit tissue in-growth. In embodiments, the average pore size diameter of the pouch is from 10 μm to 100 μm. The average thicknesses of the pouches may be varied, but preferably are from 0.4 mm to 0.8 mm. Preferably, the pouches remodel over time, and are completely replaced by in-growing tissue as the pouches degrade. Degradation of the pouch removes the need to excise a permanent polymer pouch from the implant site should the implantable medical device need to be removed, replaced or accessed. The porosity of the pouch may be tailored, for example, so that it is suitable to allow electrical grounding of an implantable medical device when needed. The new pouches may comprise one or more openings for leads, tubes or other attachments that extend from the implantable medical devices.

In embodiments, methods of production make it possible to produce nonwoven resorbable pouches for medical devices incorporating one or more bioactive agents in fewer steps, and without the use of polymer coatings. Drugs that may be incorporated into the pouches include antimicrobial agents, antibiotics, anesthetics, anti-inflammatory agents, anti-fibrotic agents, anti-scarring agents, and leukotrienes. In embodiments, methods make it possible to produce pouches comprising one or more antimicrobials, and more specifically one or more antibiotics. In a particularly preferred embodiment, the resorbable nonwoven pouches comprise rifampin and minocycline or a salt thereof, including its hydrochloride, sulfate or phosphate salt. Minocycline as used herein includes salts thereof. The pouches containing one or more bioactive agents are able to elute the bioactive agent or agents following implantation, for example, to prevent post-operative infection. In a preferred embodiment, the pouches comprising the one or more bioactive agents elute greater than 5%, 10%, or 20% by weight of the bioactive agent one day after implantation. In another embodiment, the pouches comprising the one or more bioactive agents elute greater than 10%, 20%, 30%, 40% or 50% by weight of the bioactive agent three days after implantation.

Pouches may be produced by the improved methods described herein that provide a close fit around the implantable medical devices, minimizing the dimensions of the pouch covered implantable medical device. To this end, the new pouches may be produced with smooth surfaces of low roughness on the inside of the pouches to provide a close fit, while the outer surface of the pouch is less smooth, or rougher, providing a highly porous surface that is conducive to tissue ingrowth. The new methods for producing the pouches with a smooth internal surface and a less smooth, or rougher, outer surface include covering a three-dimensional collector in the shape of an implantable medical device with resorbable polymeric spun fiber to form a pouch on the collector, and cutting an opening in the pouch to facilitate its removal from the collector.

In embodiments, a ratio of the outer surface roughness to internal surface roughness ranges from 3/2 to 3/1 and preferably about 2/1. The pouch so formed is porous, and has a smooth internal surface and a less smooth outer surface. In a particularly preferred method, a resorbable nonwoven pouch comprising one or more bioactive agents is formed in one step by spraying a three-dimensional collector with a polymeric solution comprising one or more bioactive agents, or spraying a three-dimensional collector with a polymeric solution and one or more separate solutions comprising one or more bioactive agents. In contrast, other methods for producing pouches for implantable medical devices involve fiber production, knitting or weaving of the fiber to produce a pouch, followed by coating of the pouch with a bioactive agent containing solution of polymer. The latter method, in addition to having multiple steps, does not produce a pouch that has a smooth internal surface, and a less smooth or rougher external surface.

In embodiments, the nonwoven resorbable pouches preferably have a tensile strength in any direction of 0.1 N to 100 N, and an elongation to break of 5% to 250%. If desired, the resorbable nonwoven pouches may incorporate oriented polymeric rebar in order to reinforce the pouches and increase the integrity and strength of the pouch. In one embodiment, suitable rebar is added, during formation of the pouch, to the collected fibers while the fibers are still tacky such that the rebar sticks to the pouch fibers to reinforce the pouch structure.

The nonwoven pouches are preferably made with resorbable polymers, and preferably from resorbable polymers comprising one or more of the following monomers: glycolic acid, lactic acid, trimethylene carbonate, ε-caprolactone, p-dioxanone, 3-hydroxybutyrate, 4-hydroxybutyrate, succinic acid, adipic acid, and 1,4-butanediol. Most preferably the nonwoven pouches comprise poly-4-hydroxybutyrate and copolymers thereof, or poly(butylene succinate) and copolymers thereof.

Figure 1:
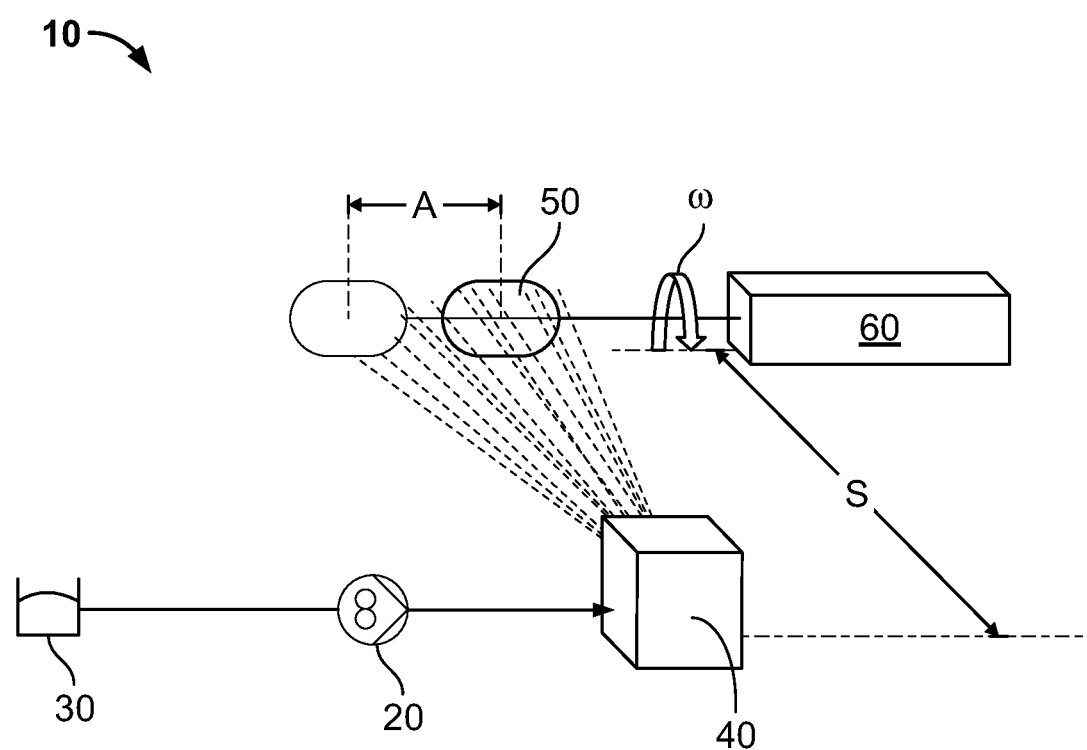
FIG. 1 is a diagram showing an equipment setup for preparing a nonwoven pouch for a pacemaker in accordance with an embodiment of the invention.

The description, objects and advantages of embodiments of the present invention will become apparent from the detailed description to follow, together with the accompanying drawings.

DETAILED DESCRIPTION OF THE INVENTION

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Last, it is to be appreciated that unless defined otherwise, all technical and scientific terms used herein have the same meaning as commonly understood by one of ordinary skill in the art to which this invention belongs.

Described herein are resorbable pouches that at least partially encase or enclose implantable medical devices that can be made in fewer steps, provide a close fit with the devices, and that do not comprise knitted or woven multifilament fibers that can trap bacteria and result in post-operative infection. Such pouches reduce the risks associated with movement of the device after implantation. Furthermore, the pouches permit tissue ingrowth as the pouch degrades to eliminate the need for surgeons to cut through the pouch if access to the implantable medical device is subsequently required or the device needs to be removed. In embodiments, one or more bioactive agents are incorporated into the pouches without adding additional manufacturing steps (such as for example a discrete or separate coating step), and without the need to use polymer coatings on the pouches. Preferably, the resorbable pouches incorporate antimicrobials or more specifically antibiotics to help reduce the incidence of post-operative infections.

I. Definitions

"Absorbable" as generally used herein means the material is degraded in the body. The terms "absorbable", "resorbable", "degradable", and "erodible", with or without the prefix "bio", can be used interchangeably herein, to describe materials broken down and gradually absorbed, excreted, or eliminated by the body.

"Atomization" as generally used herein means that a solution is broken into droplets.

"Average pore size diameter" as used herein is calculated using open source ImageJ software available at https://imagej.nih.gov/ij/index.html.

"Bioactive agent" is used herein to refer to therapeutic, prophylactic or diagnostic agents, preferably but not necessarily agents that promote healing and the regeneration of host tissue, and also therapeutic agents that prevent, inhibit or eliminate infection. "Agent" includes a single such agent and is also intended to include a plurality.

"Biocompatible" as generally used herein means the biological response to the material or device being appropriate for the device's intended application in vivo. Any metabolites of these materials should also be biocompatible.

"Blend" as generally used herein means a physical combination of different polymers, as opposed to a copolymer formed of two or more different monomers.

"Burst strength" as used herein is determined by test method ASTM D6797-02 "Standard test method for bursting strength of fabrics constant rate of extension (CRE) ball burst test," using a MTS Q-Test Elite universal testing machine or similar device, unless otherwise stated. The testing fixture uses a ⅜ inch diameter ball.

"Copolymers of poly-4-hydroxybutyrate" as generally used herein means any polymer containing 4-hydroxybutyrate with one or more different hydroxy acid units.

"Dry spinning" as used herein means a process wherein fibers are formed from a polymer solution by pumping the solution through a nozzle or spinnerets.

"Elongation to break" as used herein means the increase in length of a material that occurs when tension is applied to break the material. It is expressed as a percentage of the material's original length.

"Endotoxin units" as used herein are determined using the limulus amebocyte lysate (LAL) assay as further described by Gorbet et al. Biomaterials, 26:6811-6817 (2005).

"Melt spinning" as used herein means a process wherein polymer is melted and extruded through a spinneret to form fibers.

"Molecular weight" as used herein, unless otherwise specified, refers to the weight average molecular weight (Mw), not the number average molecular weight (Mn), and is measured by GPC relative to polystyrene.

"Nonwoven" as used herein means a fabric made not by weaving or knitting of fibers.

"Oriented" as generally used herein refers to molecular alignment of polymer chains in a material. A polymer that has been stretched becomes partly oriented and then highly oriented, and the tensile strength increases with increasing orientation. For example, an unoriented polymeric fiber may be stretched to orient the fiber which results in a polymeric fiber with higher tensile strength.

"PBS" as used herein means poly(butylene succinate).

"Poly-4-hydroxybutyrate" as generally used herein means a homopolymer containing 4-hydroxybutyrate units. It can be referred to herein as Tepha's P4HB™ polymer or TephaFLEX® biomaterial (manufactured by Tepha, Inc., Lexington, Mass.).

"Spinning" as used herein means the process of forming fibers using spinnerets or nozzles, and includes melt, centrifugal, solution, electro and dry spinning.

"Strength retention" as used herein means the amount of time that a material maintains a particular mechanical property following implantation or exposure to a particular set of conditions. For example, if the stress required to break a fiber after one month is half of its original value then the fiber is said to have a 50% strength retention after one month.

"Suture pullout strength" as used herein means the peak load (kg) at which an implant fails to retain a suture. It is determined using a tensile testing machine by securing an implant in a horizontal plate, threading a suture in a loop through the implant at a distance of 1 cm from the edge of the implant, and securing the suture arms in a fiber grip positioned above the implant. Testing is performed at a crosshead rate of 100 mm/min, and the peak load (kg) is recorded. The suture is selected so that the implant will fail before the suture fails. The suture pullout strength may be converted and expressed as Newtons.

"Tensile modulus" is the ratio of stress to strain for a given material within its proportional limit.

II. Materials for Preparing Resorbable Pouches

Described herein are pouches that at least partially encase or enclose implantable medical devices. In embodiments, the pouches are porous, allow tissue in-growth, and are replaced over time with the patient's own tissues. The pouches preferably have smooth surfaces on the inside of the pouches, and less smooth surfaces, or rougher surfaces, on the outside of the pouches. The dimensions of the pouches can be tailored to provide a close fit with different implantable medical devices. The pouches preferably comprise polymeric fibers, and more preferably are made with nonwoven resorbable fibers. The pouches preferably comprise one or more bioactive agents, and even more preferably one or more antimicrobial or antibiotic. In embodiments, the pouches so formed have an endotoxin content of less than 20 endotoxin units per device, and are sterile.

A. Polymers for Preparing Resorbable Pouches

The pouches may comprise resorbable materials, and more preferably are made completely from resorbable materials. In a preferred embodiment, the pouches are made from one or more resorbable polymers, preferably resorbable thermoplastic polymers and copolymers. The pouches may, for example, comprise a polymer or copolymer with one or more of the following monomers: glycolic acid, lactic acid, trimethylene carbonate, ε-caprolactone, p-dioxanone, 3-hydroxybutyrate, 4-hydroxybutyrate, succinic acid, adipic acid, and 1,4-butanediol. The pouches may comprise polyglycolic acid, polylactic acid, polydioxanone, polycaprolactone, copolymers of glycolic and lactic acids, poly(lactide-co-caprolactones); poly(glycolide-co-trimethylene carbonate); poly(orthoesters); polyanhydrides; poly(phosphazenes); polyhydroxyalkanoates; synthetically or biologically prepared polyesters; polycarbonates; tyrosine polycarbonates; polyamides; polypeptides; poly(amino acids); polyesteramides; poly(alkylene alkylates); polyethers; polyethylene oxide; polypropylene oxide; polyvinyl pyrrolidones; polyurethanes; polyesters; polyetheresters; polyacetals; polycyanoacrylates; poly(oxyethylene)/poly(oxypropylene) copolymers; polyketals; polyphosphates; (phosphorous-containing) polymers; polyphosphoesters; polyalkylene oxalates; polyalkylene succinates; poly(maleic acids); silk; collagen; chitin; chitosan; polysaccharides; water soluble polymers. Preferably the resorbable polymer or copolymer will be substantially or completely resorbed two years after implantation.

In another embodiment, the pouches are made from natural polymers including, for example, collagen.

Blends of polymers, preferably resorbable polymers, can also be used to prepare the resorbable pouches. Particularly preferred blends of resorbable polymers include, but are not limited to, polymers or copolymers of glycolic acid, lactic acid, trimethylene carbonate, ε-caprolactone, p-dioxanone, 3-hydroxybutyrate, 4-hydroxybutyrate, succinic acid, adipic acid, and 1,4-butanediol.

In a particularly preferred embodiment, the resorbable pouches comprise poly-4-hydroxybutyrate (Tepha's P4HB™ polymer, Lexington, Mass.) or a copolymer thereof, and can be made completely with P4HB or copolymer thereof. Copolymers include P4HB with another hydroxyacid, such as 3-hydroxybutyrate, and P4HB with glycolic acid or lactic acid monomer. P4HB is a strong, pliable thermoplastic polyester that is biocompatible and resorbable (Williams, et al. Poly-4-hydroxybutyrate (P4HB): a new generation of resorbable medical devices for tissue repair and regeneration, *Biomed. Tech.* 58(5):439-452 (2013)). Upon implantation, P4HB hydrolyzes to its monomer, and the monomer is metabolized via the Krebs cycle to carbon dioxide and water. In a preferred embodiment, the P4HB homopolymer and copolymers thereof have a weight average molecular weight, Mw, within the range of 50 kDa to 1,200 kDa (by GPC relative to polystyrene) and more preferably from 100 kDa to 600 kDa. A weight average molecular weight of the polymer of 50 kDa or higher is preferred for processing and mechanical properties.

In another preferred embodiment, the resorbable pouches comprise a polymer comprising at least a diol and a diacid. In a particularly preferred embodiment, the polymer used to prepare the resorbable pouch is poly(butylene succinate) (PBS) wherein the diol is 1,4-butanediol and the diacid is succinic acid. The PBS polymer may be a copolymer with other diols, other diacids or a combination thereof. For example, the polymer may be a PBS copolymer that further comprises one or more of the following: 1,3-propanediol, ethylene glycol, 1,5-pentanediol, glutaric acid, adipic acid, terephthalic acid, malonic acid, methylsuccinic acid, dimethylsuccinic acid, and oxalic acid. Examples of preferred copolymers are: poly(butylene succinate-co-adipate), poly(butylene succinate-co-terephthalate), poly(butylene succinate-co-butylene methylsuccinate), poly(butylene succinate-co-butylene dimethylsuccinate), poly(butylene succinate-co-ethylene succinate) and poly(butylene succinate-co-propylene succinate). The PBS polymer or copolymer may also further comprise one or more of the following: chain extender, coupling agent, cross-linking agent and branching agent. For example, PBS or copolymer thereof may be chain extended, branched or cross-linked by adding one or more of the following agents: malic acid, trimethylol propane, trimesic acid, citric acid, glycerol propoxylate, and tartaric acid. Particularly preferred agents for chain extending, branching or crosslinking the PBS polymer or copolymer thereof are hydroxycarboxylic acid units. Preferably the hydroxycarboxylic acid unit has two carboxylic groups and one hydroxyl group, two hydroxyl groups and one carboxyl group, three carboxyl groups and one hydroxyl group, or two hydroxyl groups and two carboxyl groups. In one preferred embodiment, the resorbable pouch is prepared from PBS comprising malic acid as a chain extending, branching or cross-linking agent. This polymer may be referred to as poly(butylene succinate) cross-linked with malic acid, succinic acid-1,4-butanediol-malic acid copolyester, or poly(1,4-butylene glycol-co-succinic acid), cross-linked with malic acid. It should be understood that references to malic acid and other cross-linking agents, coupling agents, branching agents and chain extenders include polymers prepared with these agents wherein the agent has undergone further reaction during processing. For example, the agent may undergo dehydration during polymerization. Thus, poly(butylene succinate)-malic acid copolymer refers to a copolymer prepared from succinic acid, 1,4-butanediol and malic acid. In another preferred embodiment, malic acid may be used as a chain extending, branching or cross-linking agent to prepare a copolymer of poly(butylene succinate) with adipate, which may be referred to as poly[(butylene succinate)-co-adipate] cross-linked with malic acid. As used herein, "poly(butylene succinate) and copolymers" includes polymers and copolymers prepared with one or more of the following: chain extenders, coupling agents, cross-linking agents and branching agents. In a particularly preferred embodiment, the PBS and copolymers thereof contain at least 70%, more preferably 80%, and even more preferably 90% by weight of succinic acid and 1,4-butanediol units. The polymers comprising diacid and diols, including PBS and copolymers thereof and others described herein, preferably have a weight average molecular weight (Mw) of 10,000 to 400,000, more preferably 50,000 to 300,000 and even more preferably 100,000 to 250,000 based on gel permeation chromatography (GPC) relative to polystyrene standards. In a particularly preferred embodiment, the polymers and copolymers have a weight average molecular weight of 50,000 to 300,000, and more preferably 75,000 to 300,000. In one preferred embodiment, the PBS or copolymer thereof used to make the resorbable pouch has one or more, or all of the following properties: density of 1.23-1.26 g/cm$^3$, glass transition temperature of −31° C. to −5° C., melting point of 111° C. to 119° C., melt flow rate (MFR) at 190° C./2.16 kgf of 2 to 10 g/10 min, and tensile strength of 30 to 60 MPa.

B. Additives

Certain additives may be incorporated into the pouches, preferably in the resorbable polymer, copolymer or blends thereof that are used to make the pouches. Preferably, these additives are incorporated into a solution that is dry spun to form the nonwoven pouch, or these additives are incorporated during a compounding process to produce pellets that can be subsequently melt-spun. For example, pellets containing additives may be extruded to produce nonwoven fibers. In a preferred embodiment, the additives are biocompatible, and even more preferably the additives are both biocompatible and resorbable.

In one embodiment, the additives may be nucleating agents or plasticizers. These additives may be added in sufficient quantity to produce the desired result. In general, these additives may be added in amounts between 1% and 20% by weight. Nucleating agents may be incorporated to increase the rate of crystallization of the polymer, copolymer or blend. Such agents may be used, for example, to facilitate fabrication of the pouch, and to improve the mechanical properties of the pouch. Preferred nucleating agents include, but are not limited to, salts of organic acids such as calcium citrate, polymers or oligomers of PHA polymers and copolymers, high melting polymers such as PGA, talc, micronized mica, calcium carbonate, ammonium chloride, and aromatic amino acids such as tyrosine and phenylalanine.

Plasticizers that may be incorporated into the compositions for preparing the pouches include, but are not limited to, di-n-butyl maleate, methyl laureate, dibutyl fumarate, di(2-ethylhexyl) (dioctyl) maleate, paraffin, dodecanol, olive oil, soybean oil, polytetramethylene glycols, methyl oleate, n-propyl oleate, tetrahydrofurfuryl oleate, epoxidized linseed oil, 2-ethyl hexyl epoxytallate, glycerol triacetate, methyl linoleate, dibutyl fumarate, methyl acetyl ricinoleate, acetyl tri(n-butyl) citrate, acetyl triethyl citrate, tri(n-butyl) citrate, triethyl citrate, bis(2-hydroxyethyl) dimerate, butyl ricinoleate, glyceryl tri-(acetyl ricinoleate), methyl ricinoleate, n-butyl acetyl rincinoleate, propylene glycol ricinoleate, diethyl succinate, diisobutyl adipate, dimethyl azelate, di(n-hexyl) azelate, tri-butyl phosphate, and mixtures thereof. Particularly preferred plasticizers are citrate esters.

C. Bioactive Agents

The pouches may comprise bioactive agents. The bioactive agents may be incorporated in or on the nonwoven structure of the pouch. For example, one or more bioactive agent may be present in or on the surface of fiber of the nonwoven pouch.

Bioactive agents may be included in the pouches for a variety of reasons. For example, bioactive agents may be included in order to improve tissue ingrowth into the implant, to improve tissue maturation, to provide for the delivery of an active agent, to improve wettability of the implant, to prevent infection, and to improve cell attachment.

The pouches may contain cellular adhesion factors, including cell adhesion polypeptides. As used herein, the term "cell adhesion polypeptides" refers to compounds having at least two amino acids per molecule that are capable of binding cells via cell surface molecules. The cell adhesion polypeptides include any of the proteins of the extracellular matrix which are known to play a role in cell adhesion, including fibronectin, vitronectin, laminin, elastin, fibrinogen, collagen types I, II, and V, as well as synthetic peptides with similar cell adhesion properties. The cell adhesion polypeptides also include peptides derived from any of the aforementioned proteins, including fragments or sequences containing the binding domains.

The pouches can incorporate wetting agents designed to improve the wettability of the surfaces of the pouch structures to allow fluids to be easily adsorbed onto the pouch surfaces, and to promote cell attachment and or modify the water contact angle of the pouch surface. Examples of wetting agents include polymers of ethylene oxide and propylene oxide, such as polyethylene oxide, polypropylene oxide, or copolymers of these, such as PLURONICS®. Other suitable wetting agents include surfactants or emulsifiers.

The pouches can contain gels, hydrogels or living hydrogel hybrids to further improve wetting properties and to promote cellular growth throughout the thickness of the pouch. Hydrogel hybrids consist of living cells encapsulated in a biocompatible hydrogel like gelatin, silk gels, and hyaluronic acid (HA) gels.

The pouches can contain active agents designed to stimulate cell ingrowth, including growth factors, cellular differentiating factors, cellular recruiting factors, cell receptors, cell-binding factors, cell signaling molecules, such as cytokines, and molecules to promote cell migration, cell division, cell proliferation and extracellular matrix deposition. Such active agents include fibroblast growth factor (FGF), transforming growth factor (TGF), platelet derived growth factor (PDGF), epidermal growth factor (EGF), granulocyte-macrophage colony stimulation factor (GMCSF), vascular endothelial growth factor (VEGF), insulin-like growth factor (IGF), hepatocyte growth factor (HGF), interleukin-1-B (IL-1 B), interleukin-8 (IL-8), and nerve growth factor (NGF), and combinations thereof.

Other bioactive agents that can be incorporated in the implants include antimicrobial agents, in particular antibiotics, antiseptics, disinfectants, oncological agents, anti-scarring agents, anti-inflammatory agents, anesthetics, small molecule drugs, anti-angiogenic factors and pro-angiogenic factors, immunomodulatory agents, and blood clotting agents. The bioactive agents may be proteins such as collagen and antibodies, peptides, polysaccharides such as chitosan, alginate, hyaluronic acid and derivatives thereof, nucleic acid molecules, small molecular weight compounds such as steroids, inorganic materials such as ceramics and hydroxyapatite, or complex mixtures such as platelet rich plasma.

In a preferred embodiment, the pouches comprise one or more antimicrobials or antibiotics. Antimicrobials include copper, zinc, silver, and gold. Any antibiotics suitable for use in a human may be incorporated into the pouches. As used herein, "antibiotic" means an antibacterial agent. The antibacterial agent may have bateriostatic or bacteriocidal activities. Nonlimiting examples of classes of antibiotics that may be incorporated into the pouches include tetracyclines (e.g. minocycline), rifamycins (e.g. rifampin), macrolides (e.g. erythromycin), penicillins (e.g. nafcillin), cephalosporins (e.g. cefazolin), other beta-lactam antibiotics (e.g. imipenem, aztreonam), aminoglycosides (e.g. gentamicin), chloramphenicol, sulfonamides (e.g. sulfamethoxazole), glycopeptides (e.g. vancomycin), quinolones (e.g. ciprofloxacin), fusidic acid, trimethoprim, metronidazole, clindamycin, mupirocin, polyenes (e.g. amphotericin B), azoles (e.g. fluconazole) and beta-lactam inhibitors (e.g. sulbactam). Nonlimiting examples of specific antibiotics that may be used include erythromycin, erythromycin ethyl succinate, erythromycin ethylcarbonate, erythromycin glucoheptanoate, erythromycin stearate, erythromycin lauryl sulfate propionate, erythromycin lactobionate, triacetyl oleandomycin, oleandomycin phosphate, amikacin sulfate, bekanamycin sulfate, aminodeoxykanamycin, kanamycin monosulfate, tobramycin, acetyl kitasamycin, kitasamycin, kitasamycin succinate, kitasamycin tartarate, chloramphenicol, chloramphenicol alginine succinate, chloramphenicol sodium succinate, chloramphenicol stearate, chloramphenicol morpholinoacetate, chloramphenicol palmitate, chloramphenicol stearoylglycolate, chloramphenicol sulfate morpholinoacetate, colistin hydrochloride, colistin, colistin sodium methane sulfonate, colistin sulfate, josamycin, josamycin propionate, dihydrostreptomycin hydrochloride, dihydrostreptomycin sulfate, compound streptomycin, streptomycin hydrochloride, streptomycin calcium chloride hydrochloride, streptomycin sulfate, streptomycin isoniazone sulfate, cephacetrile sodium, cephazolin sodium, cephapyrin sodium, cephalexin, cephaglycin, cephalothin sodium, cephaloridine, ceftezol sodium, cephradine, oxytetracycline hydrochloride, oxytetracycline, oxytetracycline calcium, chlorotetracycline hydrochloride, chlorotetracycline, tetracycline hydrochloride, rolitetracycline nitrate, tetracycline L-methylene-lysine, tetracycline methaphosphate, rolitetracycline, dimethylchlorotetracycline hydrochloride, dimethylchlorotetracycline, doxycycline hydrochloride, minocycline hydrochloride, metacycline hydrochloride, actinomycin D, azalomycin F, amphotericin B, enbiomycin sulfate, enramycin hydrochloride, aureothricin, capreomycin sulfate, carzinophilin, carbomycin, gramicidin, gramicidine S hydrochloride, griseofulvin, chromomycin A3, gentamycin sulfate, cycloserin, sarkomycin, siccanin, dibekacin sulfate, acetylspiramycin, spiramycin, spectinomycin hydrochloride, daunorubicin hydrochloride, doxorubicin hydrochloride, trichomycin, nystatin, neocarzinostatin, novobiocin calcium, novobiocin sodium, viomycin sulfate, bacitracin, variotin, paromomycin sulfate, pimaricin, pyrrolnitrin, fusidate sodium, fradiomycin palmitate, fradiomycin sulfate, bleomycin hydrochloride, bleomycin sulfate, ampicillin, ampicillin sodium, talampicillin hydrochloride, carbenicillin sodium, carbenicillin indanyl sodium, carbenicillin phenyl sodium, phenoxymethylpenicillin, phenoxymethylpenicillin potassium, phenoxymethylpenicillin calcium, phenoxymethylpenicillin benzathine, penicillin potassium, penicillin sodium, penicillin procaine, benzylpenicillin potassium, benzylpenicillin sodium, benzylpenicillin procaine, benzylpenicillin benzathine, compound penicillin potassium, compound benzylpenicillin potassium, compound benzylpenicillin sodium, compound benzylpenicillin benzathine, clindamycin, clindamycin hydrochloride, clindamycin palmitate hydrochloride, lincomycin hydrochloride, amoxicillin, oxacillin sodium, cloxacillin sodium, cyclacillin, dicloxacillin sodium, sulbenicillin sodium, pivmecillinam hydrochloride, phenethicillin potassium, flucloxacillin sodium, propicillin potassium, hetacillin potassium, methicillin sodium, pentamycin, polymyxin B sulfate, mitomycin C, maridomycin propionate, mikamycin, midecamycin, rifampicin, rifampin, ribostamycin sulfate, pyrrolenitrin, actinomycin, bleomycin, daunorubicin, doxorubicin and neocarzinostatin. Aminoglucosides and polymyxins are preferred to use, because they have strong alkalinity and a high antibiotic action to microbes which cause urinary tract infection. As the antiseptics and disinfectants, it is preferred to use dyestuff medical preparations such as acrinol or acriflavine, etc., furan medical preparations such as nitrofurazone, etc., cationic soap medical preparations such as benzalkonium chloride or benzethonium chloride, etc., cyclohexidine, povidone-iodine, minocycline, nafcillin, cefazolin, imipenem, aztreonam, gentamicin, sulfamethoxazole, vancomycin, ciprofloxacin, trimethoprim, metronidazole, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, fluconazole, itraconazole and ketoconazole.

It is desirable that the antibiotic(s) selected kill or inhibit the growth of one or more bacteria that are associated with infection following surgical implantation of an implantable medical device. Such bacteria are recognized by those of ordinary skill in the art and include *Staphylococcus aureus* and *Staphylococcus epidermis*. Preferably, the antibiotic(s) selected are effective against strains of bacteria that are resistant to one or more antibiotic. To enhance the likelihood that bacteria will be killed or inhibited, it may be desirable to combine one or more antibiotic. It may also be desirable to combine one or more antibiotic with one or more antiseptic. It will be recognized by one of ordinary skill in the art that antimicrobial agents having different mechanisms of action or different spectrums of action may be most effective in achieving such an effect. In a particularly preferred embodiment, the pouches comprise rifampin and minocycline, or salt thereof. Minocycline salts include minocycline hydrogen chloride.

If desired, the bioactive agent may be in or on a vehicle adapted to release the bioactive agent. For example, in embodiments, the bioactive agent may be embedded, coated, mixed, dissolved or dispersed on or in a vehicle that is incorporated on or into the pouch. The vehicle may be used to provide a particular release profile of the one or more bioactive agents.

In a preferred embodiment, the pouches comprising the one or more bioactive agent(s) elute greater than 5%, 10%, or 20% by weight of the bioactive agent(s) one day after implantation. In another embodiment, the pouches comprising the one or more bioactive agents elute greater than 10%, 20%, 30%, 40% or 50% by weight of the bioactive agent(s) three days after implantation. In a further embodiment, the pouches comprising the one or more bioactive agents elute greater than 30%, 40%, 50%, 60% or 70% by weight of the bioactive agent(s) seven days after implantation.

D. Nonwovens

The pouches may be formed of, or comprise, nonwovens. The nonwovens are preferably made from resorbable polymers, preferably resorbable thermoplastic polymers, and even more preferably from resorbable thermoplastic polyesters. The nonwovens are preferably made from the polymers listed herein. In a particularly preferred embodiment, the nonwoven is made from P4HB or copolymer thereof, or PBS or copolymer thereof.

The inward facing side of the nonwoven pouch (the side that faces the implantable medical device) is preferably smoother than the outward facing side of the pouch (the side facing tissues that surround the implantable medical device) allowing a pouch to be formed that fits tightly around the implantable medical device. The average surface roughness ($R_a$), as measured by stylus profilometry, of the inward facing side of the pouch ranges from 0.5 and 20 microns, preferably from 1 to 15 microns, and even more preferably from 5 to 10 microns. In contrast, the average surface roughness ($R_a$) of the outward facing side of the pouch is between from 23 and 50 microns, preferably from 23 to 35 microns, and even more preferably from 25 to 30 microns. In one embodiment, the nonwoven pouch has an average surface roughness of 25.6 microns on the outward facing surface and an average surface roughness of 9.4 microns on the inward facing surface as described in Example 2, herein. In another embodiment, the difference in average surface roughness between the outward and inward facing surfaces of the nonwoven is 10-20 microns.

In embodiments, a ratio of the outer surface roughness to internal surface roughness ranges from 3/2 to 3/1 and preferably about 2/1.

The average thickness of the nonwovens used to prepare the pouches is preferably less than 5 mm, 4 mm, 3 mm, or 2 mm, but greater than 10 µm, but more preferably the average thickness of the nonwoven is from 0.1 to 1 mm, and even more preferably from 0.4 to 0.8 mm.

The average diameter of the nonwoven fibers is preferably from 0.01 µm to 100 µm, more preferably from 0.1 µm to 20 µm, and even more preferably from 1 µm to 10 µm. The nonwoven fibers are preferably unoriented or partially oriented, or a combination thereof. The fibers may be oriented randomly in the nonwoven, or the fibers may be more substantially oriented in one direction than another direction such that the nonwoven has anisotropic properties with higher tensile strength in one direction than another direction. The tensile strength of the nonwoven in any direction is preferably from 0.01 N to 1,000 N, and more preferably from 0.1 N to 100 N. In an embodiment, the burst strength of the nonwoven is from 0.01 Kgf to 50 Kgf, and more preferably from 0.1 Kgf to 5 Kgf. The elongation to break of the nonwoven is preferably from 5% to 250%, and more preferably 40% to 100%.

It is desirable that the nonwoven is sufficiently porous to allow tissue ingrowth in order for a pouch made from the nonwoven to anchor the implantable medical device at the implantation site and prevent migration of the implantable medical device. It is also desirable that the nonwoven is sufficiently porous to allow electrical grounding of an implantable medical device at least partially enclosed or encased in a pouch made from the nonwoven. The average pore size of the nonwoven is preferably from 1 µm to 10 mm, more preferably from 10 μm to 1 mm, and even more preferably from 10 μm to 100 μm.

The fibers of the nonwoven preferably degrade after implantation in less than 5 years, and more preferably in less than 2 years. In a particularly preferred embodiment, the nonwoven degrades in a period of 1 week to 18 months after implantation.

E. Rebar

In embodiments, the base material forming the pouch is reinforced with a material having different properties (e.g., a greater tensile strength). Preferably, this rebar-like component is used to reinforce the nonwoven structure of the pouch. The rebar is preferably made from a resorbable material, preferably a resorbable thermoplastic polymer. The rebar is preferably made from the polymers listed herein. In a particularly preferred embodiment, the rebar is made from P4HB or copolymer thereof.

One suitable form of rebar is resorbable polymeric fiber. Preferably the resorbable polymeric fiber is oriented (meaning that the fiber has been stretched during processing), either partially or fully, so that it has higher tensile strength than unoriented polymeric fiber. The average diameter of the rebar fibers is preferably from 10 μm to 1 mm, more preferably from 20 μm to 500 μm, and even more preferably from 50 μm to 200 μm. A particularly preferred partially or fully oriented resorbable polymeric fiber to reinforce the nonwoven of the pouch is made from P4HB or copolymer thereof, or alternatively, from PBS or copolymer thereof.

III. Methods of Manufacturing Resorbable Pouches for Implantable Medical Devices.

A. Pouches Formed from Nonwoven

The pouches that at least partially enclose or encase implantable medical devices may comprise the nonwovens disclosed herein. In a preferred embodiment, the nonwoven pouches are formed by dry spinning. A suitable equipment setup for dry spinning nonwoven comprises (i) a reservoir for a polymer solution, (ii) a pump, preferably a metering pump, connected to a nozzle or spinneret, and (iii) a collector for collecting the nonwoven fibers. A preferred method of forming the resorbable pouches by dry spinning comprises: (a) dissolving the polymer to be dry spun in a volatile solvent; (b) optionally filtering the solution; (c) pumping the solution to a spraying nozzle or spinneret, optionally through a filter; (d) atomizing the solution through the nozzle or spinneret and allowing the solvent to evaporate to form fine fibers, optionally by applying heat; (e) collecting the solidified fibers on a collector, preferably wherein the collector is rotating about an axis and back and forth along the axis, and removing the pouch from the collector.

The solvent used in the dry spinning process may be selected from volatile solvents that are able to dissolve the selected polymer. Examples of volatile solvents include: chloroform, methylene chloride, acetone, tetrahydrofuran (THF), ethyl acetate, methyl acetate, diethylether, 1,4-dioxane, hexane, ethanol, and acetonitrile, and combinations thereof, including THF-methanol, 1,4-dioxane-methanol, and acetone-methanol. The concentration of the polymer in the solvent solution will depend upon the solubility of the polymer in the chosen solvent, and the viscosity of the polymer solution. Preferably, the concentration of the polymer in the solvent solution is between 0.5 and 30% (wt/vol), and more preferably 3-10% (wt/vol). Preferably the viscosity of the polymer solution is between 1 and 100 centipoise (cP), more preferably between 2.5 and 55 cP. The weight average molecular weight of the polymer can be selected to provide an optimum polymer solution viscosity and fiber/nonwoven strength. Typically, suitable polymer weight average molecular weights range from 10 kDa to 600 kDa, and more preferably 50 kDa to 400 kDa.

In a preferred embodiment, the collector is connected to a bar which in turn is connected to a motor that can rotate the collector in either direction, and also move the collector back and forth in an axial direction. These movements of the collector make it possible to evenly apply the dry spun nonwoven fiber to the collector so that the pouch has a relatively even thickness in all areas. The use of a motor to rotate the collector also makes it possible to produce pouches with anisotropic properties, such as a higher tensile strength in one direction than another direction. Pouches with anisotropic properties can be produced by moving the scaffold consistently in one direction, for example, by rotating the collector continuously in one direction. The anisotropic properties of the pouch may be increased by increasing the speed of the movement of the collector, for example, by rotating the collector faster in one direction. In an embodiment, the pouches have a tensile strength in one direction that is 10% higher than the tensile strength of the pouch in a different direction.

The equipment setup can also be configured so that the collector is stationary, and the nozzle or spinneret is moving around the collector to coat the nonwoven fibers on the collector.

The collector is preferably of the same size and shape as the implantable medical device. Examples of implantable medical devices such as CRM devices and their dimensions are described in US 2008/0132922 to Buevich, incorporated herein by reference in its entirety.

In a preferred embodiment, the surface of the collector is smooth. Use of a collector with a smooth surface makes it possible to produce a pouch with a smooth internal surface, and a less smooth external surface. A smooth internal pouch surface provides a larger contact area with a tight fit and minimizes movement of the implantable medical device inside the pouch, and a less smooth external pouch surface provides a structure that allows tissue ingrowth into the pouch. The pouch so formed in this embodiment does not substantially increase the size of the implantable medical device when the implantable medical device is placed in the pouch and the combination is implanted, and at the same time the outer pouch surface makes it possible to form a tissue pocket for the implantable medical device that will tightly secure the device in position. That is, the tissue pocket formed by ingrowing tissue into the pouch will not be substantially larger than the exterior of the implantable medical device, or contain unwanted voids, but rather the tissue pocket formed around the device will provide a close fit. In one embodiment, the collector is made from a stainless metal alloy. In a preferred embodiment, the collector is made from aluminum.

Pouches formed by dry spinning of polymer solutions preferably have nonwoven fibers with average diameters preferably from 0.01 μm to 100 μm, more preferably from 0.1 μm to 10 μm, and even more preferably from 1 μm to 10 μm. The pouch fibers are preferably unoriented or partially oriented, or a combination thereof.

In embodiments, the pouches comprise fibers that are bonded together thermally or chemically, and not interlaced or woven. Preferably, the portions of the fibers are fused together and overlap in an arrangement that provides the pouch properties (including, for example, the strength, surface roughness, and porosity) described herein.

In order to encourage tissue ingrowth into the nonwoven pouch and allow electrical grounding of an implantable medical device, the pouch is formed with a nonwoven that is sufficiently porous to allow the ingrowth of cells and passage of fluid. The average pore size of the nonwoven pouch structure is preferably from 1 μm to 10 mm, more preferably from 10 μm to 1 mm, and even more preferably from 10 μm to 100 μm.

Without intending to being bound to theory, the thickness of the nonwoven fibers that need to be collected to form a pouch with sufficient strength to at least partially encase or enclose an implantable medical device, and form a suitable tissue pocket in vivo for the device will depend upon the properties of the fibers as well as the size and weight of the implantable medical device. The average thickness of the nonwoven is preferably less than 5 mm, 4 mm, 3 mm, or 2 mm, but greater than 10 μm, but more preferably the average thickness of the nonwoven is from 0.1 to 1 mm, and even more preferably from 0.4 to 0.8 mm. The tensile strength of the nonwoven pouch in any direction is preferably from 0.01 N to 1,000 N, and more preferably from 0.1 N to 100 N. In an embodiment, the burst strength of the nonwoven pouch is from 0.01 Kgf to 50 Kgf, and more preferably from 0.1 Kgf to 10 Kgf. The tensile strength and burst strength of the porous nonwoven pouch are selected by control of the: flow rate (ml/min of polymer solution), diameter of the orifice(s) of the nozzle or spinneret, distance between the nozzle or spinneret and the collector, temperature, collection time, choice of polymer solvent, viscosity of the polymer solution, weight average molecular weight of the polymer, and pumping pressure.

Once a pouch with a suitable thickness has been formed at the collector, the pouch may be removed from the collector by placing a small slit in the pouch. For example, a small slit may be placed in the pouch using a sharp instrument, such as a sharp knife, and then the pouch removed from the collector. Ideally, the size of the slit is just sufficient to remove it from the collector, and to insert the implantable medical device.

The strength of the pouch may optionally be further increased by the addition of rebar to the pouch during the manufacturing process. In one embodiment, resorbable polymeric rebar, as described above, may be applied to the nonwoven structure of the pouch while the nonwoven fibers are still slightly tacky. This allows the rebar to bind to the nonwoven fibers, and provide reinforcement of the nonwoven pouch. One or more layers of rebar may be applied to the pouch to reinforce the pouch, and layers of rebar may be coated with one or more further layers of nonwoven fibers. The size of the rebar will depend on the size of the pouch. Suitable rebar includes oriented resorbable polymeric fibers that are 0.1 cm to 5 cm in length, and more preferably 0.5 cm to 2 cm in length. Preferably, the polymer of the rebar and the nonwoven are the same.

FIG. 1 shows a suitable equipment setup 10 for preparing a pacemaker pouch in accordance with one embodiment of the invention. However, it is to be understood that the same equipment setup can be used to prepare pouches for other types of implantable medical devices, and different equipment setups may be used to produce a pacemaker pouch except where recited in the appended claims.

With reference again to FIG. 1, a gear pump 20 is used to pump a polymer solution 30 to a spraying nozzle 40. The polymer solution 30 is atomized as it leaves the nozzle 40, and fine polymer fibers are deposited on the collector 50. The collector 50 may be a pacemaker collector, and have the shape of a pacemaker as described herein.

A motor 60 attached to the pacemaker collector 50 via a rod is used to rotate the pacemaker collector (w), and move it axially (A), as shown by the arrows in FIG. 1. The spraying distance (S) between the spraying nozzle and pacemaker collector is adjusted to optimize the properties of the nonwoven collected on the pacemaker collector. Additionally, in embodiments, the motor 60 is able to rotate the collector 50 both clockwise and counterclockwise.

In one preferred embodiment, the pouches that at least partially enclose or encase implantable medical devices comprise nonwoven made from P4HB or copolymer thereof. These pouches are preferably formed from volatile solutions of P4HB or copolymer thereof. Preferably, the pouches are formed from chloroform solutions comprising P4HB or copolymer thereof, and even more preferably wherein the concentration of P4HB or copolymer thereof is 0.5-30% (wt/vol). A particularly preferred concentration is 5-10% (wt/vol). After dissolving the polymer in chloroform, the polymer solution is preferably filtered prior to dry spinning the solution. A preferred viscosity range for the polymer solution in chloroform is 100 mPa·s to 10,000 mPa·s, but more preferably 500 mPa·s to 2,000 mPa·s. The equipment setup shown in FIG. 1 is suitable for dry spinning solutions of P4HB or copolymer thereof. In one embodiment, a pouch comprising P4HB is prepared from a chloroform solution of P4HB (8% wt/vol), using a spraying distance of 50 cm, a pump pressure of 450 kPa (4.5 bar), and with the collector moving back and forth across the collector in an axial movement at 350 mm/min and rotating at a rate of 300 rpm. In order to obtain a pouch with a substantially uniform thickness of P4HB nonwoven, the collector is rotated both clockwise and counterclockwise. A P4HB pouch with an average thickness of 500-600 μm is obtained by rotating the collector 15 times in each direction, i.e. alternating rotation of the collector in the clockwise and counterclockwise directions until the collector is coated 15 times in each direction.

Figure 2:
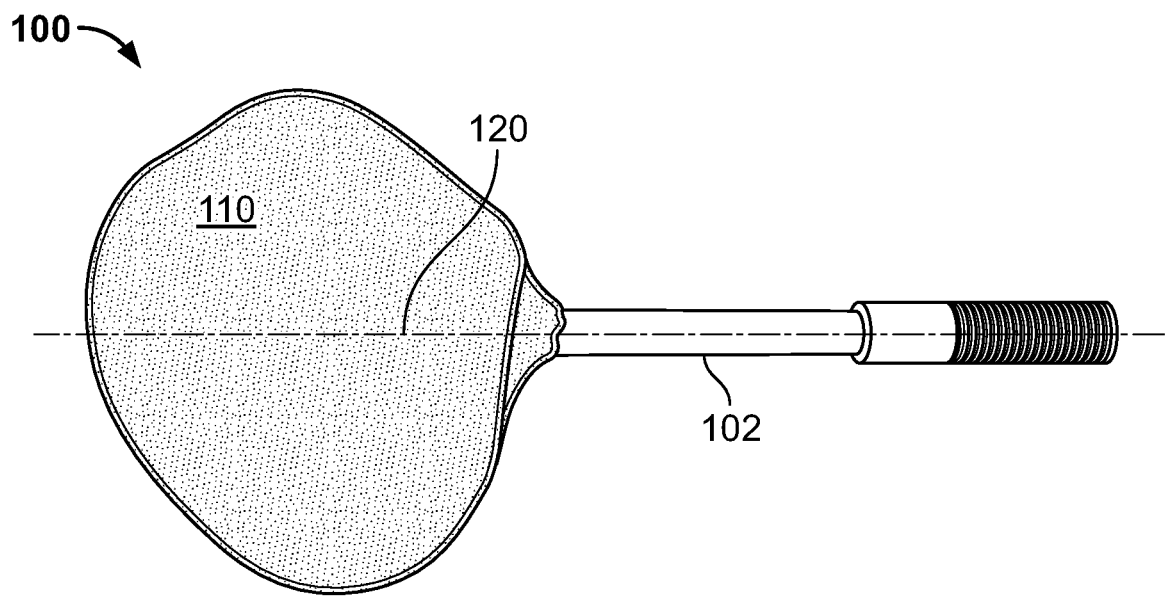
FIG. 2 illustrates a collector in the shape of a pacemaker that has been encased by a pouch of resorbable nonwoven fiber in accordance with an embodiment of the invention.

FIG. 2 shows a pacemaker collector 100 having deposited thereon P4HB dry spun fibers to form a pacemaker pouch 110. The collector is connected to a rod 102, and has an axis 120 about which the collector is rotated by the motor.

Pouches produced by the dry spinning method disclosed herein have very low levels of residual solvent, which is important for any implantable device. The P4HB pouch shown in FIG. 2 was tested by MHE-GC/MS (Multiple headspace extraction—gas chromatography/mass spectrometry) for the presence of residual solvent. No residual solvent could be detected. The detection limit for residual chloroform in the P4HB pouch by MHE-GC/MS was 0.4 ppm.

The nonwoven pouch may also be formed from collagen. In one embodiment, a collagen pouch may be electrospun. In an embodiment, the collagen pouch may be electrospun from an acetic acid solution of collagen, and optionally cross-linked. The collagen may be cross-linked with glutaraldehyde or formaldehyde.

The nonwoven pouch may also be formed from PBS or copolymer thereof, including succinic acid-1,4-butanediol-malic acid copolyester. In an embodiment, the pouch may be dry spun or electrospun from volatile solutions of poly (butylene succinate) or copolymer thereof. Preferably, the pouches are formed from chloroform solutions or dichloromethane solutions comprising PBS or copolymer thereof, and even more preferably wherein the concentration of PBS or copolymer thereof is 0.5-30% (wt/vol). In another embodiment, the pouches may be electrospun from dimethylformamide (DMF) or dimethylsulfoxide (DMSO) solutions comprising PBS or copolymer thereof. DMF and DMSO may be used as co-solvents with other solvents, including chloroform and dichloromethane. Other solvents that may be used to solution process PBS or copolymer thereof to form the nonwoven pouches include THF, 1,4-dioxanone and acetone.

B. Pouches Comprising Bioactive Agents

In a preferred embodiment, pouches comprise one or more bioactive agents. In embodiments, the bioactive agents are incorporated into the pouch by dry spinning using one or more solutions comprising one or more bioactive agents.

In one embodiment, the bioactive agent or agents are dissolved in the same polymer solution as the base material, and dry spun to form a pouch comprising the one or more bioactive agents.

In an alternative embodiment, the one or more bioactive agents may be dissolved in a second solvent, and co-spun with the base polymer solution to form a pouch comprising one or more bioactive agents. In the event that two or more bioactive agents are to be incorporated in the pouch and they are not soluble in the same solvent, then separate solutions of the bioactive agents may be prepared and dry spun simultaneously with the polymer solution, or a first bioactive agent may be included in the polymer solution and co-spun with a solution containing a second bioactive agent. By "co-spinning" it is meant that the pouch is formed using two or more nozzles or spinnerets fed by two or more solutions comprising polymer, bioactive agents, antimicrobials or antibiotics. For example, a pouch comprising an antibiotic is formed by co-spinning of a solution of polymer through one nozzle or spinneret, and a second solution of an antibiotic through a second nozzle or spinneret. Co-spinning includes spinning with different solutions at the same time or alternating between one solution and one or more different solutions. For example, a pouch comprising an antibiotic is formed by spinning a polymer solution for a period of time, followed by spinning a solution comprising an antibiotic solution, and repeating this process as many times as necessary.

In a particularly preferred embodiment, the pouch is dry spun from one solution of P4HB that further comprises one or more bioactive agents, more preferably one or more antimicrobial agents, and even more preferably one or more antibiotics. Examples of bioactive agents, antimicrobial agents and antibiotics that may be incorporated in the P4HB solution are listed herein. The P4HB polymer and one or more bioactive agents, antimicrobial agents or antibiotics are preferably dissolved in chloroform, methylene chloride, acetone, THF or 1,4-dioxane. However, if the one or more bioactive agents, antimicrobial agents or antibiotics are not soluble in any of those solvents, a co-solvent is used. Suitable co-solvents include methanol, water and ethanol. Thus, solutions of one or more bioactive agents, antimicrobial agents or antibiotics in methanol, water or ethanol, may be added to solutions of P4HB, for example, P4HB dissolved in THF, 1,4-dioxane, chloroform, or acetone. These solvent systems, for example, THF-methanol, 1,4-dioxane-methanol, chloroform-methanol, and acetone-methanol, comprising P4HB and one or more bioactive agents, antimicrobial agents or antibiotics, are then dry spun to form pouches comprising bioactive agents, antimicrobials or antibiotics.

In a preferred embodiment, a P4HB pouch comprising rifampin and minocycline is formed by dry spinning a solution comprising P4HB, rifampin and minocycline. The solvent is preferably selected from the group comprising: THF-methanol, 1,4-dioxane-methanol, acetone-methanol or chloroform-methanol. In one embodiment, a solution of minocycline in methanol is added to a solution of P4HB and rifampin in THF, 1,4-dioxane, chloroform or acetone. The solution of P4HB and rifampin may also comprise methanol as a co-solvent. Preferably, the amount of methanol in the co-solvent system is the minimum amount required to solubilize minocycline at the desired concentration. Ideally, the amount of methanol in the P4HB solution to be dry spun is less than 30% (vol/vol), more preferably less than 20% (vol/vol), and even more preferably less than 10% (vol/vol). One preferred solvent system for dry spinning P4HB nonwovens comprising rifampin and minocycline is a ratio of 1,4-dioxane to methanol of 95:5 (vol/vol). In a particularly preferred embodiment, the dry spinning solution is formed to provide a dry spun P4HB pouch comprising 1-100 mg of rifampin and 1-100 mg of minocycline, but more preferably 1-10 mg of rifampin and 1-10 mg of minocycline. In another embodiment, a P4HB pouch comprising rifampin and minocycline is formed by dry spinning a solution comprising P4HB and optionally rifampin, and co-spinning a solution of minocycline and optionally rifampin.

In an embodiment, a pouch is formed from a solution comprising 1 (wt/vol) P4HB and 0.2% (wt/vol) antibiotics in a co-solvent system of methanol/dioxane (38%/62% vol/vol).

In another preferred embodiment, the pouch is dry spun from one solution of PBS or copolymer thereof that further comprises one or more bioactive agents, more preferably one or more antimicrobial agents, and even more preferably one or more antibiotics. Examples of bioactive agents, antimicrobial agents and antibiotics that may be incorporated in the solution of PBS or copolymer thereof are listed herein. The PBS or copolymer thereof and one or more bioactive agents, antimicrobial agents or antibiotics are preferably dissolved in chloroform, methylene chloride, acetone, THF or 1,4-dioxane, or combinations thereof. However, if the one or more bioactive agents, antimicrobial agents or antibiotics are not soluble in any of those solvents, a co-solvent is used. Suitable co-solvents include methanol, water and ethanol. Thus, solutions of one or more bioactive agents, antimicrobial agents or antibiotics in methanol, water or ethanol, may be added to solutions of PBS or copolymer thereof, for example, PBS or copolymer thereof dissolved in THF, 1,4-dioxane, methylene chloride, chloroform, or acetone. These solvent systems, for example, THF-methanol, 1,4-dioxane-methanol, chloroform-methanol, and acetone-methanol, methylene chloride-methanol, comprising PBS or copolymer thereof and one or more bioactive agents, antimicrobial agents or antibiotics, are then dry spun to form pouches comprising bioactive agents, antimicrobials or antibiotics.

In a preferred embodiment, a pouch comprising PBS or copolymer thereof, rifampin and minocycline is formed by dry spinning a solution comprising PBS or copolymer thereof, rifampin and minocycline. The solvent is preferably selected from the group comprising: THF-methanol, 1,4-dioxane-methanol, acetone-methanol, methylene chloride-methanol, or chloroform-methanol. In one embodiment, a solution of minocycline in methanol is added to a solution of PBS or copolymer thereof and rifampin in THF, 1,4-dioxane, chloroform or acetone. The solution of PBS or copolymer thereof and rifampin may also comprise methanol as a co-solvent. Preferably, the amount of methanol in the co-solvent system is the minimum amount required to solubilize minocycline at the desired concentration. Ideally, the amount of methanol in the solution of PBS or copolymer thereof to be dry spun is less than 30% (vol/vol), more preferably less than 20% (vol/vol), and even more preferably less than 10% (vol/vol). One preferred solvent system for dry spinning nonwovens of PBS or copolymer thereof comprising rifampin and minocycline is a ratio of 1,4-dioxane to methanol of 95:5 (vol/vol). In a particularly preferred embodiment, the dry spinning solution is formed to provide a dry spun pouch comprising PBS or copolymer thereof and 1-100 mg of rifampin and 1-100 mg of minocycline, but more preferably 1-10 mg of rifampin and 1-10 mg of minocycline. In another embodiment, a pouch comprising PBS or copolymer thereof, rifampin and minocycline is formed by dry spinning a solution comprising PBS or copolymer thereof and optionally rifampin, and co-spinning a solution of minocycline and optionally rifampin.

Although it is preferred that the pouches comprising one or more bioactive agents, one or more antimicrobials or one or more antibiotics are formed in one step by dry spinning for reasons discussed herein, in another embodiment, the bioactive agents, one or more antimicrobials or one or more antibiotics are applied in a second step to the pouches by depositing a second polymer comprising these agents on the surface of the pouch. In this embodiment, the pouch may be formed from the same polymer as the second polymer, for example P4HB, PBS or copolymer thereof, or other polymer listed herein, or a different polymer. In the latter case, the structure of the pouch is formed from a first polymer, and a second polymer solution comprising one or more bioactive agents is deposited on the pouch structure formed by the first polymer. The second polymer is preferably a polymer listed herein. The second polymer can be a carrier for the one or more bioactive agents. The second polymer can be used to control the rate of release of the one or more bioactive agents from the pouch. If desired, the properties of the second polymer can be modified by introducing a third polymer or another additive, including those listed herein. In an embodiment, a P4HB pouch or pouch comprising PBS or copolymer thereof, is dry spun and a polymer solution comprising one or more bioactive agents, one or more antimicrobial agents or one or more antibiotics, including rifampin and minocycline, is deposited on the pouch.

The polymer coating comprising one or more bioactive agents, one or more antimicrobial agents or one or more antibiotic may be applied to the pouch, for example, by solution spraying or solution deposition.

C. Pouches Comprising Other Features

In an embodiment, the pouch may further comprise a means to close the pouch after insertion of the implantable medical device. One suitable means is a drawstring. A drawstring may be sewn around the edge of the opening of the nonwoven pouch, and drawn tight after insertion of an implantable medical device in the pouch.

In another embodiment, the pouch may further comprise a means to secure the pouch in place at the time of implantation, and prior to tissue ingrowth. One suitable means to secure the pouch in place is to incorporate a tether into the pouch that a surgeon can suture or staple to prevent the pouch from moving immediately after implantation. In one embodiment, a tether is sewn to the pouch, glued to the pouch, or welded to the pouch. The tether is preferably a thread.

In another embodiment, the pouch may further comprise a means to apply slight pressure to the implantable medical device to prevent the movement of the device within the pouch. Pressure may be applied to the implantable medical device by incorporating into the pouch a resorbable elastic component with elastic recovery between 1 and 100%, more preferable between 1 and 50%. The resorbable elastic component may be incorporated into the body of the pouch, for example, during production of the nonwoven fiber structure, or it may be incorporated as a sealed attachment to the periphery of the pouch. Examples of resorbable elastic components that can be incorporated into the pouch include copolymers of 3-hydroxybutyrate and 4-hydroxybutyrate with a co-monomer ratio of 30:70, and polyurethanes.

IV. Methods of Implanting and Expanding

Embodiments of the invention include implanting a medical device in a patient. Initially, an implantable medical device is placed inside the pouches. Preferably, a resorbable nonwoven pouch is provided for encapsulating the medical device, the pouch having a smoother inside surface relative to the exterior surface.

The assembly of an implantable medical device and a pouch is then implanted in a patient in need thereof. The implantable medical device is positioned in the pouch in a manner that allows any leads, catheters, tubes or similar attachments to extend from the pouch. The implantable medical device/pouch is preferably implanted in a subcutaneous site. Leads, catheters, tubes or similar attachments extending from the pouch are implanted in other subcutaneous sites or placed deeper into the body, for example, into organs, inside vessels, in the brain or spine, or other implantation sites. The assembly of the pouch containing the implantable medical device is generally implanted at a surgically prepared site, usually referred to as a "pocket". The preparation of the surgical site is performed in a sterile field. The pouch and the implantable medical device are preferably sterilized in suitable containers prior to implantation, or are sterilized prior to implantation. In one embodiment, the implantable medical device/pouch is implanted in a prepectoral position. In another embodiment, the implantable medical device/pouch is implanted under the skin of the upper abdomen. To minimize the risk of introducing microbes into the implantation site, or pocket, it is preferable to apply disinfectants or antiseptics to the skin around the implantation site prior to surgery. Optionally, antimicrobial agents may also be applied directly to the implantation site, and the patient may also be prescribed antibiotics during the recovery period.

Implantable medical devices are inserted into the pouches generally through slits or openings present in the pouches. The assembly so formed is then implanted. Alternatively, the slit or opening is sealed prior to implantation of the assembly, except around a small opening for leads, catheters, tubes and similar attachments protruding from the implantable medical device. In one embodiment, the slit or opening of the pouch is sealed by tightening a draw cord, or sewing a thread around the opening in the pouch, except in both cases allowing the leads, catheters, tubes or other attachments of the implantable medical devices to protrude from the pouch.

EXAMPLES

The present invention will be further understood by reference to the following non-limiting examples.

Example 1

Manufacture of Resorbable Nonwoven P4HB Pouch

A resorbable nonwoven P4HB pouch to at least partially enclose or encase an implantable medical device was prepared using the equipment setup shown in FIG. 1 as follows. Poly-4-hydroxybutyrate was dissolved in chloroform to form a solution with a concentration of 8% (wt/vol). The polymer solution was filtered to remove any particulate. The viscosity of the solution used to make the pouch was between 900 and 2,000 mPa·s. The polymer solution was conveyed to the spraying nozzle shown in FIG. 1 using a gear pump with a flow rate of 3.2 ml/min. The P4HB polymer solution was atomized at a pressure of 450 kPa (4.5 bar), and fiber collected at a spraying distance of 50 cm measured between the nozzle and the collector. The collector was made from aluminum, and had a smooth surface. The collector was rotated at 300 rpm in clockwise and counter-clockwise directions a total of 15 times, and the collector was simultaneously moved back and forth axially a distance "A" of 5 cm as shown in FIG. 1 at a speed of 350 mm/min to ensure uniform fiber deposition.

Figure 3:
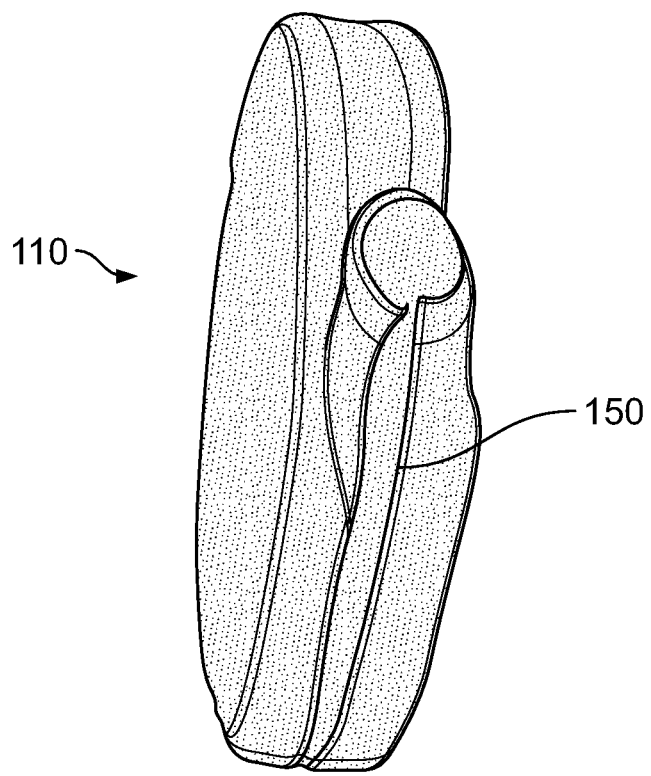
FIG. 3 illustrates a pouch for a pacemaker made from a resorbable nonwoven with an opening slit on the edge of the pouch for insertion of a pacemaker in accordance with an embodiment of the invention.

FIG. 2 shows the collector 100, in the shape of a pacemaker, that had been rotated about the axis 120 indicated in FIG. 2, and moved back and forth axially, to produce a pouch on the collector evenly coated with P4HB fibers. The pouch 110 was removed from the collector by cutting a slit 150 in the edge of the pouch to allow removal of the pouch from the collector, as shown in FIG. 3. The pouch so obtained had a smooth internal surface, and a less smooth external surface.

The thicknesses of three pouches were determined according to USP-NF standard 24 by measuring the thicknesses of each pouch in eight different locations. The measuring device had a diameter of 11.3 mm, and a contact pressure of 166±3 g/cm$^2$. The thicknesses of the pouches were in the range of 550-603 µm. The fiber diameter medians were measured by SEM, and found to be 1.75-2.23 µm. The pore sizes were determined for two different pouches according to ASTM F 316-03. The minimum pore sizes were in the range of 8.6-12.3 µm. The frequency of pores with a size below 20 µm for both pouches was above 80%.

Figure 4:
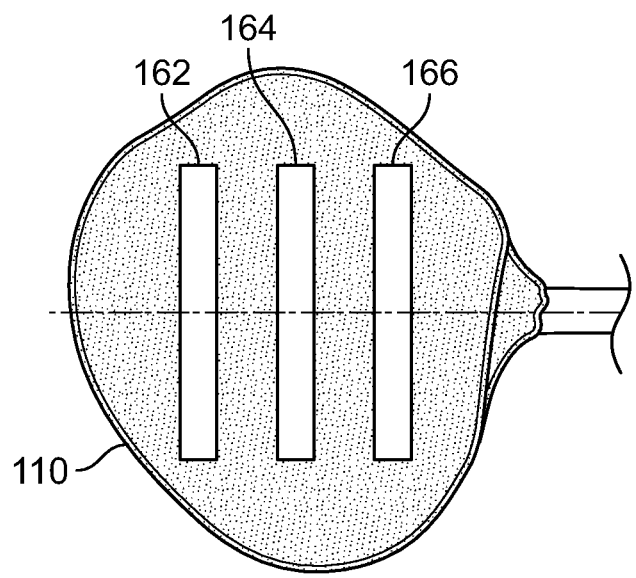
FIG. 4 is an illustration of a collector in the shape of a pacemaker that has been encased by a pouch of resorbable nonwoven showing three locations of test samples cut from the pouch to test mechanical properties of the pouch in the fiber direction in accordance with an embodiment of the invention.
Figure 5:
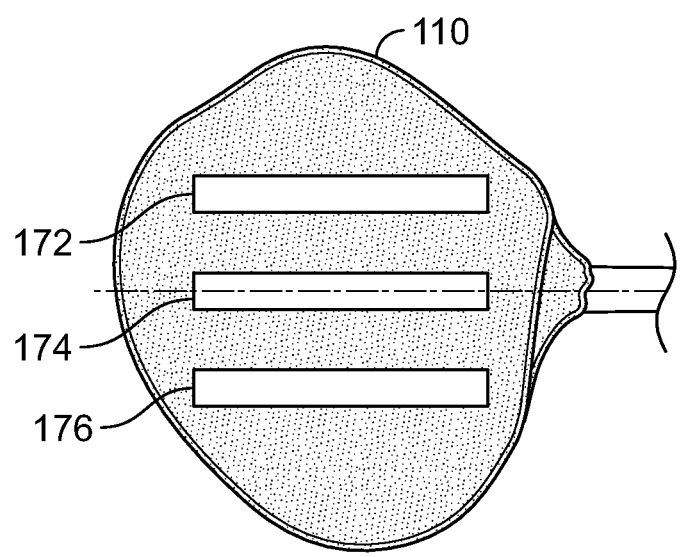
FIG. 5 is another illustration of a collector in the shape of a pacemaker that has been encased by a pouch of resorbable nonwoven showing the three locations of test samples cut from the pouch to test mechanical properties of the pouch in the cross-fiber direction in accordance with an embodiment of the invention.

The tensile strength and elongation at break of the pouch were determined, according to DIN EN 29073 part 3, for test samples cut from the pouch in the fiber direction and the cross-fiber direction. Test areas 162, 164, 166 cut from one side of the pouch in the fiber direction are shown in FIG. 4, and test areas 172, 174, 176 in the cross-fiber direction are shown in FIG. 5. The test samples measured 20 mm in length and 0.5 mm in width. A total of 6 samples were tested from each pouch (3 in the rotational axis direction and 3 in the opposite direction). In the fiber direction, the average maximum tensile strength of the pouch was 6.7 N, and the average elongation at break was 117%. In the cross-fiber direction, the average maximum tensile strength of the pouch was 4.6 N, and the average elongation at break was 110%. The results show that the tensile strength and elongation at break of the pouch is higher in the fiber direction than the cross-fiber direction.

The residual solvent in the pouches after drying the pouches under vacuum for 30 min at 40° C. was determined by MHE-GC/MS (Multiple headspace extraction—gas chromatography/mass spectrometry). The level of residual solvent in the pouch was below the limit of quantitation. The limit of quantitation was 0.4 ppm.

Example 2

Determination of the Roughness of the Internal and External Pacemaker Pouch Surfaces The smoothness of the outwardly facing surface and the inwardly facing surfaces of the pacemaker pouch prepared in Example 1 were determined using stylus profilometry with the following equipment setup: Veeco Dektak D150 with a 12.5 µm stylus tip and 1.0 mg of force. Prior to the analysis, the vertical accuracy of the equipment was verified using a reference material with a nominal 100 nm step height standard, Veeco S/N301-028-2-06. Two outwardly facing samples and two inwardly facing samples from the pouch were prepared for analysis by affixing them to a glass slide using thin double-sided adhesive tape. Surface roughness measurements were taken by scanning the samples. The area scanned in each case was 1 cm$^2$ and each scan lasted 90 seconds. The surface roughness ($R_a$) of the outwardly facing samples were 24.1 and 27.0 microns, and the surface roughness ($R_a$) of the inwardly facing samples were 9.0 and 9.8 microns. On average, the surface roughness ($R_a$) of the outwardly facing sample was 25.6 microns, and the surface roughness ($R_a$) of the inwardly facing sample was 9.4 microns. The measurements demonstrate that the inwardly facing surface of the pacemaker pouch prepared in Example 1 is smoother than the outwardly facing surface of the pouch.

Modifications and variations of the methods and compositions will be apparent from the foregoing detailed description and are intended to come within the scope of the appended claims.

The invention claimed is:

1. A porous resorbable implantable pouch formed of nonwoven polymeric fibers, the pouch adapted to at least partially enclose an implantable medical device, comprising an inside surface and an outside surface, wherein the inside surface of the pouch is smooth having an average roughness from 1 to 15 microns measured by stylus profilometry, the outside surface of the pouch is rougher than the smooth inside surface, and wherein a ratio of outside surface roughness to inside surface roughness is from 3/2 to 3/1.

2. The pouch of claim 1, wherein the implantable medical device is selected from the group consisting of: breast implant, cardiac rhythm management device, pacemaker, defibrillator, pulse generator, implantable access system, muscle and nerve stimulators, ventricular assist device, gastric stimulators, infusion pump, drug pump, neurostimulator, vagal nerve stimulator, spinal cord neuromodulator, deep brain stimulator, and sacral nerve stimulator.

3. The pouch of claim 1, wherein the pouch has at least one of the following properties: (i) a plurality of pores with average diameters between 10 µm and 100 µm, (ii) an average thickness of 0.4 to 0.8 mm, (iii) a tensile strength in any direction of 0.1 N to 100 N, and (iv) an elongation to break of 5% to 250%.

4. The pouch of claim 1, wherein the pouch further comprises resorbable polymeric oriented fiber rebar to reinforce the pouch.

5. The pouch of claim 1, wherein the pouch further comprises at least one bioactive agent.

6. The pouch of claim 5, wherein greater than 5% by weight of the at least one bioactive agent is released one day after the pouch is implanted in a patient.

7. The pouch of claim 5, wherein the at least one bioactive agent is selected from the group consisting of: antimicrobial agent, anesthetic, anti-inflammatory agent, anti-fibrotic agent, anti-scarring agent, leukotriene, silver, chlorhexidine, vancomycin, cephalosporin, gentamicin, triclosan, rifampin, tetracycline, minocycline or salt thereof, minocycline hydrochloride, COX-1 inhibitor, COX-2 inhibitor, and derivatives thereof.

8. The pouch of claim 5, wherein the at least one bioactive agent is present inside the fibers of the pouch.

9. The pouch of claim 1, wherein the fibers of the polymeric pouch comprise one or more of the following polymers: polylactic acid; polyglycolic acid; copolymers of glycolic and lactic acids; polycaprolactone; poly(orthoester); polyanhydride; poly(phosphazene); polyhydroxyalkanoate; poly-3-hydroxybutyrate; poly-3-hydroxybutyrate-co-3-hydroxyvalerate; poly-4-hydroxybutyrate; poly-3-hydroxybutyrate-co-4-hydroxybutyrate; poly-3-hydroxybutyrate-co-3-hydroxyhexanoate; polycarbonate; tyrosine polycarbonate; polyester, polyimide, polyesteramide; poly(dioxanone); poly(alkylene alkylate); poly(butylene succinate) or copolymer thereof, succinic acid-1,4-butanediol-malic acid copolyester, polyether; polyethylene oxide, polypropylene oxide; polyvinyl pyrrolidone; polyurethane; polyetherester; polyacetal; polycyanoacrylate; polyketal; polyphosphate; polyphosphoester; polyalkylene oxalate; polyalkylene succinate; poly(maleic acid); and collagen.

10. The pouch of claim 1, wherein the fibers of the polymeric pouch comprise a polymer with at least one of the following monomers: glycolic acid; lactic acid; trimethylene carbonate; c-caprolactone; p-dioxanone; 3-hydroxybutyrate; 4-hydroxybutyrate; succinic acid; adipic acid; and 1,4-butanediol.

11. The pouch of claim 1, wherein the pouch is produced by a method comprising the steps of: (i) covering a three-dimensional collector with polymeric spun fibers, (ii) cutting an opening in the pouch, and (iii) removing the pouch from the collector.

12. The pouch of claim 11, wherein the method further comprises at least one of the following steps: (a) the collector is rotated about an axis, and moved back and forth along an axis to cover the collector with polymeric fibers, (b) the polymeric spun fibers are dry spun, electrospun, or melt spun, and (c) the polymeric spun fibers comprise at least one bioactive agent.

13. The pouch of claim 1, wherein the pouch is formed by one of the following steps: (i) spinning a solution of poly-4-hydroxybutyrate containing rifampin and minocycline or salt thereof, (ii) co-spinning separate solutions of poly-4-hydroxybutyrate, rifampin and minocycline or a salt thereof, (iii) co-spinning a solution of poly-4-hydroxybutyrate and a solution of rifampin and minocycline or salt thereof, and (iv) co-spinning a solution of poly-4-hydroxybutyrate and rifampin and a solution of minocycline or salt thereof, or spinning the solutions of (i)-(iv) wherein poly-4-hydroxybutyrate is replaced by poly(butylene succinate) or copolymer thereof.

14. An implantable medical pouch for at least partially enclosing an implantable medical device, the pouch comprising a drug-eluting, nonwoven, resorbable porous material, the pouch further comprising an inside surface and an outside surface, and wherein the inside surface of the pouch is smooth having an average roughness from 1 to 15 microns measured by stylus profilometry, the outside surface of the pouch is rougher than the smooth inside surface, and wherein a ratio of outside surface roughness to inside surface roughness is from 3/2 to 3/1, and wherein the drug is incorporated into the material such that the drug elutes from the bulk of the pouch.

* * * * *

UNITED STATES PATENT AND TRADEMARK OFFICE
CERTIFICATE OF CORRECTION

PATENT NO. : 11,612,754 B2
APPLICATION NO. : 16/553651
DATED : March 28, 2023
INVENTOR(S) : Skander Limem et al.

Page 1 of 1

It is certified that error appears in the above-identified patent and that said Letters Patent is hereby corrected as shown below:

In the Specification

At Column 18, Line 20, replace "1" with --1%--

Signed and Sealed this
Twenty-third Day of May, 2023

Katherine Kelly Vidal
*Director of the United States Patent and Trademark Office*